United States Patent [19]
Wickes

[11] Patent Number: 5,585,874
[45] Date of Patent: Dec. 17, 1996

[54] COLOR IMAGING CONVERGENCE PROJECTOR

[75] Inventor: George L. Wickes, Rochester, N.Y.

[73] Assignee: Bausch & Lomb Incorporated, Rochester, N.Y.

[21] Appl. No.: 371,625

[22] Filed: Jan. 12, 1995

[51] Int. Cl.⁶ ............................... A61B 3/02; A61B 3/00
[52] U.S. Cl. .......................... 351/233; 351/223; 351/246
[58] Field of Search ................................... 351/223, 222, 351/204, 200, 213, 219, 220, 221, 233, 234, 235, 236, 246, 247, 242, 160 R, 162, 163, 216, 217, 218

[56] References Cited

U.S. PATENT DOCUMENTS

| | | | |
|---|---|---|---|
| 3,479,937 | 11/1969 | Sullivan | 95/11 |
| 3,801,188 | 4/1974 | Hunt et al. | 351/30 |
| 3,804,528 | 4/1974 | Kilmer et al. | 356/165 |
| 3,876,293 | 4/1975 | Ramos | 350/305 |
| 5,024,520 | 6/1991 | Akiyama | 351/221 |
| 5,050,966 | 9/1991 | Berman | 359/38 |
| 5,129,716 | 7/1992 | Holakovszky | 351/50 |

Primary Examiner—Hung Xuan Dang
Attorney, Agent, or Firm—Katherine McGuire

[57] ABSTRACT

Color imaging projection apparatus for projecting a pair of laterally spaced, collimated, colored light beams onto the iris portion of an individual's eyes while viewing him/herself in a two-way mirror. A housing is provided wherein is located a light source, a color wheel, a pair of laterally spaced, optical collimating rods, and a front-surfaced mirror. Light from the light source passes through a selected color filter of the color wheel, through the optical collimating rods which transmit two discreet, colored beams of light onto the front-surfaced mirror which, in turn, directs the beams of colored light through the two-way mirror to the individual located on the opposite side thereof. The individual positions him/herself with the colored light beams impinging the iris portion of their eyes as the individual views him/herself in the two-way mirror. The invention is useful in marketing colored contact lenses in that it enables an individual to visualize him/herself with different colored eyes without the need for application of trial colored lenses onto the individual's eyes.

13 Claims, 4 Drawing Sheets

COLOR IMAGING CONVERGENCE PROJECTOR

BACKGROUND OF THE INVENTION

The present invention relates to image projection apparatus and, more particularly, to image projection apparatus which includes a two-way mirror and means for selectively projecting one of a plurality of colors through the mirror and onto the eyes of a person viewing him/herself in the mirror. The invention has utility in that the color projected through the mirror may be focused onto just the iris portions of the person's eyes so that the person may see what they look like with an eye color different from their natural eye color. The invention is thus especially useful in the colored contact lens business.

Colored contact lenses (of both prescription and non-prescription types) which alter the natural color of a person's eyes have seen increasing popularity in recent years. Since customers understandably want to see what they look like with different colored eyes prior to purchasing these types of lenses, clinicians heretofore needed to carry try-on sets of such lenses for their customers to place on their eyes and make their selection amongst the different colored lenses available. Due to sanitary and regulatory concerns, the try-on sets are disposed of immediately following a single customer's try-on of the lenses. Since a single customer can go through potentially the full array of colored try-on lenses available at a single visit, the cost of providing try-on lenses to all customers can be considerable.

There thus exists a need for a relatively inexpensive, easy and quick method by which a colored contact lens customer can realistically visualize him/herself with different colored eyes as an aid to the colored lens selection process.

SUMMARY OF THE INVENTION

The present invention eliminates the need for try-on lenses by providing an apparatus and method for projecting a selected color directly onto the iris of a customer's eyes while the customer is viewing him/herself in a two-way mirror. More particularly, a projection apparatus is provided which includes a light source and a color wheel having a plurality of colors representing the full choice of colors in which colored contact lenses are offered for sale. The projection apparatus further includes a pair of laterally spaced optical collimating rods with the color wheel being positioned between the light source and the rods. The rods are positioned to direct two spaced collimated beams of colored light at a first surface of the mirror whereby a customer viewing him/herself in the opposite surface of the mirror may position him/herself with the colored beams impinging directly onto the iris of each of their eyes.

The effect of the two-way mirror (also known in the art as a 50% mirror) is such that the customer sees only him/herself with the color of their irises changed to the color transmitted through the mirror by the eye rods from the opposite side thereof. Color wheel moving means are provided for the customer to select the desired color for projection onto their eyes. Optical rod moving means are provided for adjusting the IPD (Inter-Pupilary Distance) to closely approximate the true IPD of a particular customer's eyes. As such, a customer may quickly select a desired color by moving the color wheel, make the necessary IPD adjustment to the optical rods, and position him/herself in front of the mirror such that the color beams transmitted through the mirror impinge directly onto their irises. Once the IPD is adjusted, the customer may quickly and easily switch between all the colors of the color wheel. The color beams transmitted through the mirror merge with their own natural iris color which closely approximates the color the customer's eyes would be if they were actually wearing lenses of the same color as transmitted by the color wheel and optical rods.

DETAILED DESCRIPTION OF THE PREFERRED EMBODIMENT

Figure 1:
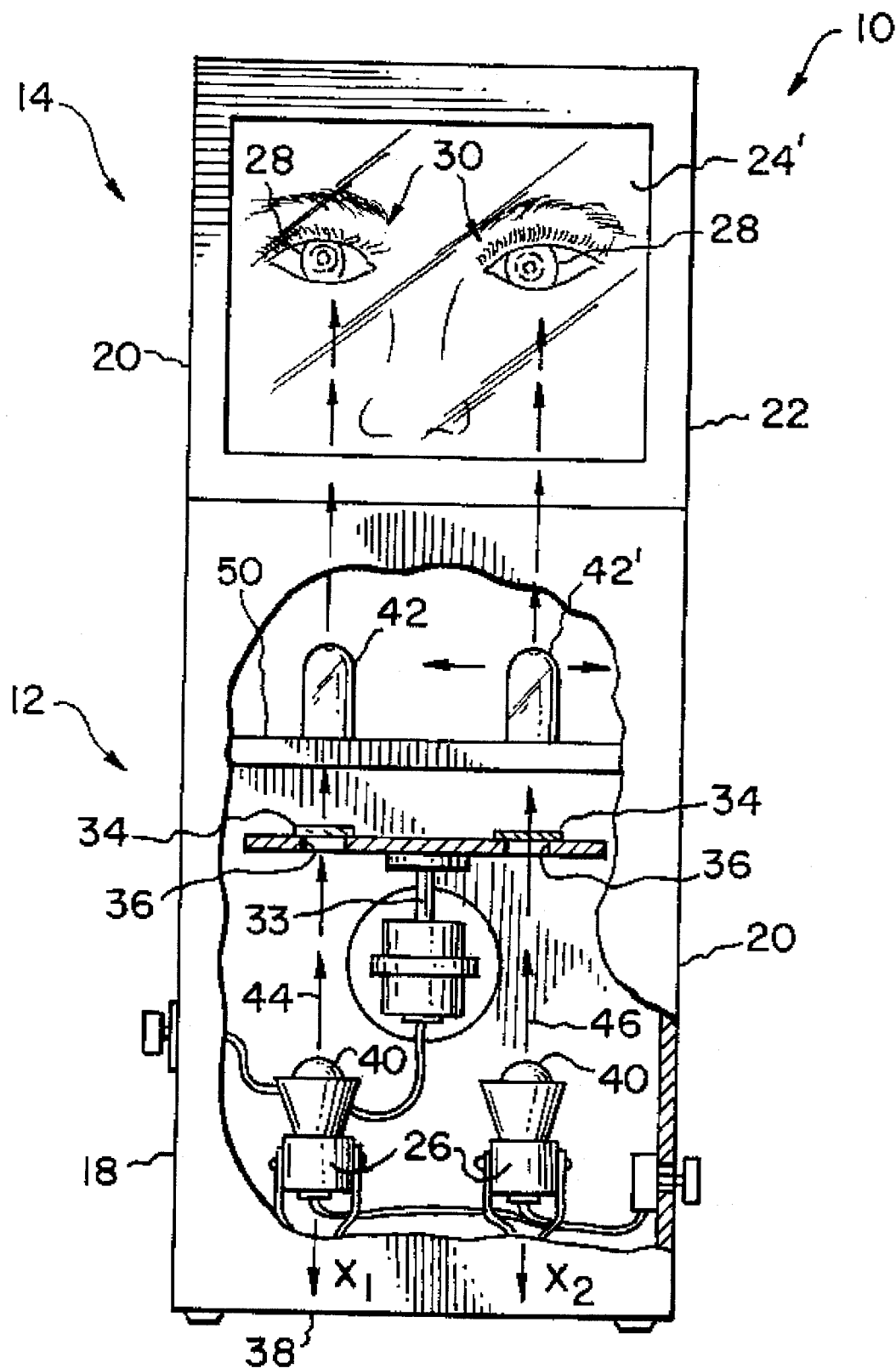
FIG. 1 is a front elevational view of the apparatus of the invention with selected portions thereof broken away to reveal internal components thereof.
Figure 2:
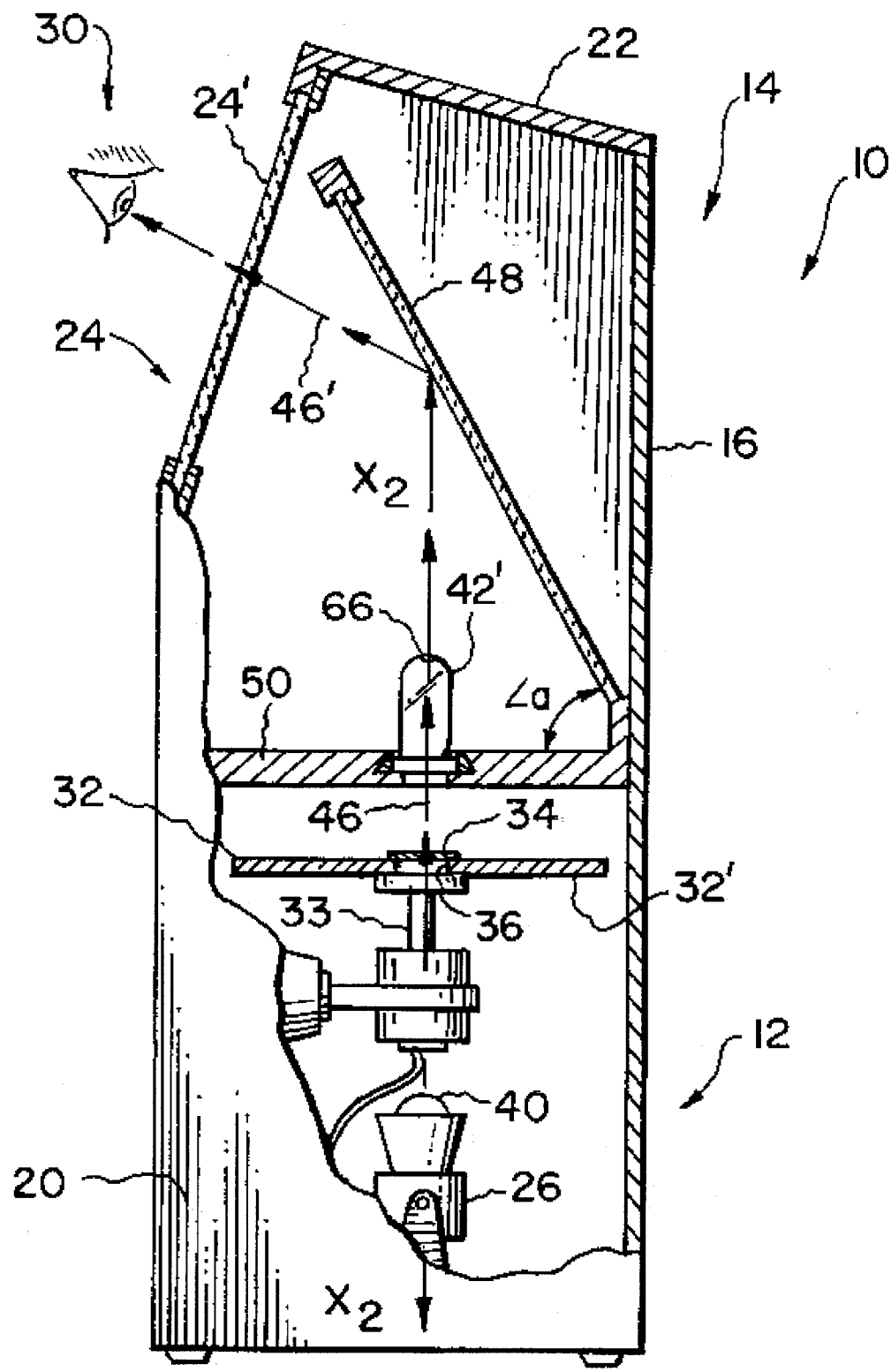
FIG. 2 is a side elevational view thereof with selected portions thereof shown in cross-section.

Referring now to the drawing, there is seen in FIGS. 1 and 2 a color imaging projection apparatus designated generally by the reference numeral 10. Projection apparatus 10 generally comprises a box-like housing structure having a base portion 12 and upper-structure 14 sharing a common rear wall 16 and opposite side walls 18 and 20. A two-way mirror 24 forms a front wall of the upper-structure 14 of apparatus 10, with mirror 24 being set at an angle with respect to rear wall 16 and a top housing wall 22 so that a customer positioned in front of apparatus 10 may easily view him/herself in mirror 24.

As mentioned above, mirror 24 is a two-way mirror which reflects only 50% of surrounding artificial and ambient light rays while permitting the remaining 50% of the surrounding light rays to pass therethrough. As such, mirror 24 may transmit light rays therethrough from one side thereof to the other, while remaining visually indistinguishable from a 100% reflective mirror. It is assumed the area surrounding the exterior of apparatus 10 where customers are located is relatively brightly lit, while the light source 26 positioned interiorly of apparatus 10 is set at a predetermined intensity level which is lower than the exterior light intensity.

Apparatus 10 is operable to project a preselected color onto just the iris portions 28 of a customer's eyes 30, with the customer being positioned in front of apparatus 10 while viewing him/herself in the outwardly facing surface 24' of mirror 24. More particularly, a color wheel 32 is rotatably mounted upon a motor-driven shaft 33 in a substantially horizontal plane within base portion 12, and includes a plurality of individual color filters 34 which cover a respective plurality of apertures 36 arranged in annularly spaced relation thereabout. A light source is provided within base 12 which preferably comprises a pair of laterally spaced lamps 26 positioned adjacent bottom wall 38 of base 12 below color wheel 32. The light bulbs 40 of lamps 26 are directed to impinge light emanating therefrom upon the bottom surface 32' of color wheel 32 such that a portion of the light emitted by lamps 26 passes through the color filters 34 positioned vertically thereover.

A pair of optical collimating rods 42 and 42' are provided directly vertically above lamps 26 with color wheel 32 positioned therebetween such that any two diametrically opposite color filters 34 on wheel 32 may be positioned along the vertical axes $X_1$ and $X_2$ along which light beams 44 and 46 travel. As seen best in FIG. 2, a 100% (fully reflective), front-surface mirror 48 is positioned between the rear and top walls 16 and 22 of upper-structure 14 at an acute angle "a" with respect to a support surface 50 dividing the upper-structure 14 from the base portion 12. The 100% mirror 48 is provided to reflect light beams 44 and 46 passing through rods 42 and 42' onto two-way mirror 24 as seen best in FIG. 2. The term "front-surface" for mirror 48 means the reflective coating is on the front surface of the mirror (facing two-way mirror 24) which prevents distorting "ghost" images from being reflected thereby.

As previously mentioned, the spacing between the optical rods 42 and 42' and, hence, the color beams 44' and 46' as reflected by front-surface mirror 48, may be adjusted to closely approximate the true IPD of the customer. In this regard, attention is directed to FIGS. 3–5 which show one of the rods 42 as being fixed while the other rod 42' is movable with respect thereto. More particularly, both rods 42 and 42' are supported within apparatus 10 by horizontally extending support surface 50 which lies in a plane substantially spaced and parallel to bottom wall 38. Fixed rod 42 extends through and is frictionally secured in a hole 52 formed in support surface 50 and which is of the same circumference outline as rod 42. Movable rod 42', however, extends through and is frictionally secured in a hole 54 formed in a dovetailed sliding block 56 which is longitudinally slidable within a dovetailed groove 58 formed in support surface 50 such that rod 46' is movable laterally of rod 42. An elongated opening 60 formed in groove 58 permits light beam 46 to pass through support surface 50 which proceeds through hole 54 and rod 42' regardless of the location of block 56 in groove 58. A stop 62 is provided to limit the distance block 56 may be moved toward rod 42, with this distance being the minimum IPD any one customer would be expected to have (e.g, 50 mm). The maximum distance between rods 42 and 42' is limited on the opposite side by side wall 22, with the total IPD adjustable distance being preferably about 25 mm.

Figure 3:
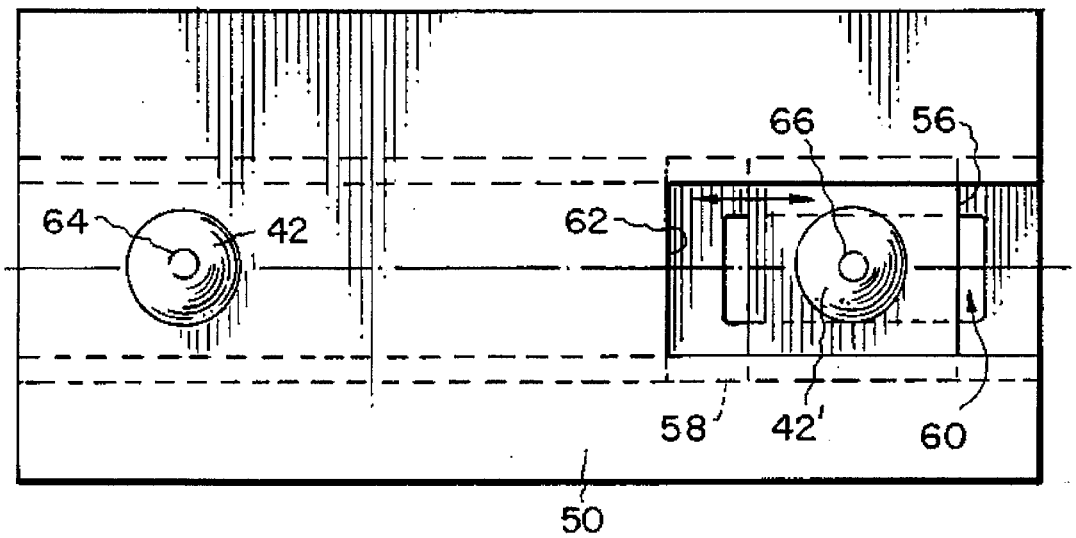
FIGS. 3 and 4 are top plan views of the optical rods and IPD adjustment means therefor.
Figure 4:
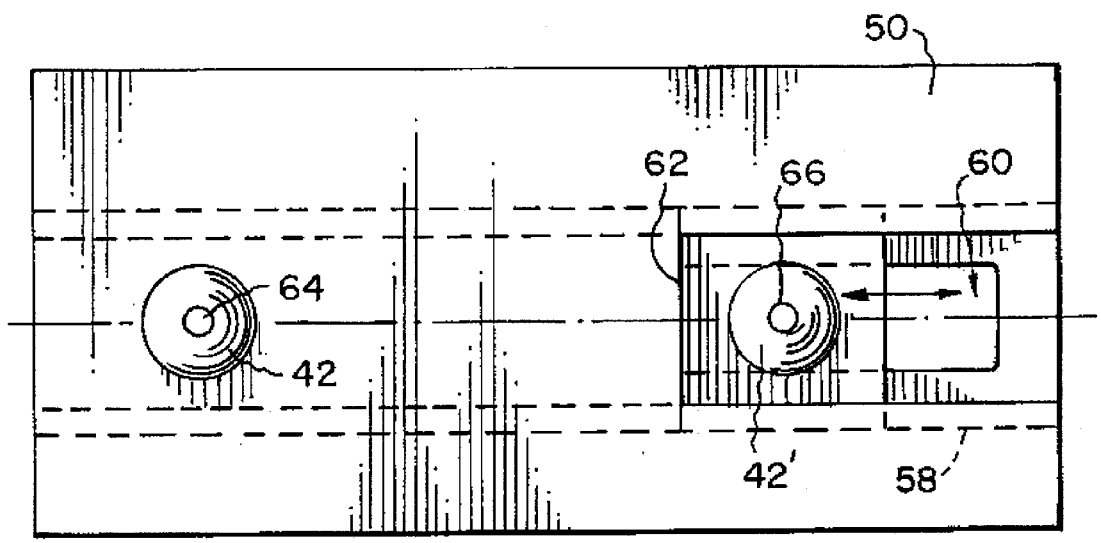
Figure 5:
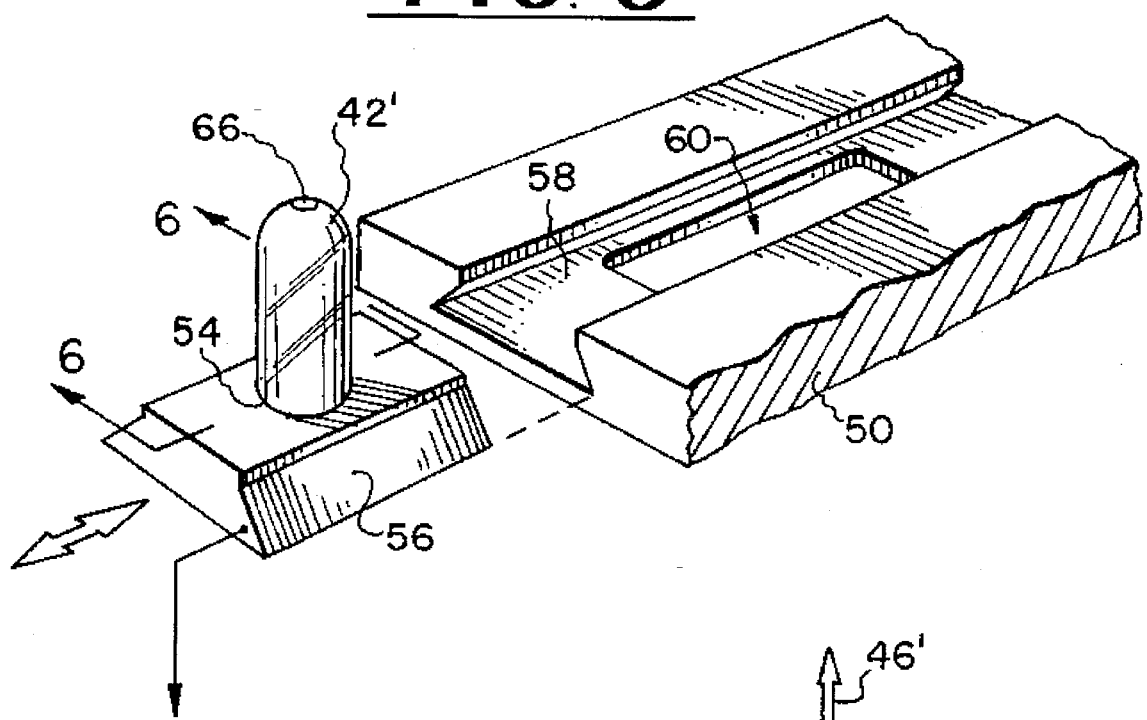
FIG. 5 is a perspective view of the movable optical rod shown removed from the sliding block mounting for clarity.
Figure 6:
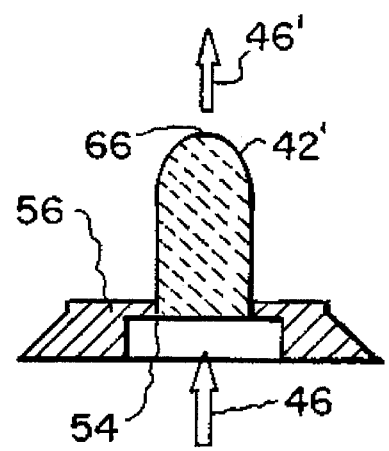
FIG. 6 is a cross-sectional view of the optical rod and sliding block.

As seen best in the plan views of FIGS. 3 and 4, eye rods 42 and 42' are of elliptical outline about their circumference. This is so that the light beams 44' and 46' collimated and emitted thereby will closely match the shape of a customer's irises 28 when their eye lids are in a relaxed yet open state as seen in FIG. 1. As such, the colored light beams 44' and 46' striking their irises 28 will act to color only that portion of their eyes thereby closely approximating the visual effect a colored contact lens would create if it were placed directly on the eye. Also, it may be desired to black out the corresponding pupil region of each colored beam 44' and 46' by applying an opaque covering 64 and 66 of relatively small diameter onto the tips of rods 42 and 42', respectively.

What is claimed is:

1. Apparatus for projecting colored light onto the iris portions of an individual's eyes comprising:
    a) a light source;
    b) a two-way mirror having first and second surfaces;
    c) at least one color filter positioned between said light source and said two-way mirror; and
    d) optical collimating means for collimating and directing at least one discreet light beam, as emitted by said light source and colored by said at least one color filter, through said two-way mirror from said first to said second surface thereof whereby an individual viewing him/herself in said second surface of said two-way mirror is able position him/herself with said at least one collimated, colored light beam striking their iris.

2. The apparatus of claim 1, and further comprising a front-surfaced mirror positioned for directing said at least one light beam from said collimating means to said two-way mirror.

3. The apparatus of claim 1 wherein said optical collimating means comprises a transparent optical rod.

4. The apparatus of claim 3, and further comprising a first and second transparent optical rods arranged in laterally spaced relation to one another, said first and second transparent optical rods being operable to collimate and emit a first and second, colored light beams from said light source to and through said two-way mirror.

5. The apparatus of claim 4, and further comprising means for adjusting the lateral distance between said first and second transparent optical rods.

6. The apparatus of claim 5, wherein said lateral adjusting means comprises a slide block upon which one of said first and second transparent optical rods is mounted.

7. The apparatus of claim 6, and further comprising a mounting surface upon which said first and second transparent optical rods are positioned, said lateral adjusting means further including an elongated groove wherein said sliding block engages for selective movement towards and away from the other of said one of said first and second transparent optical rods.

8. The apparatus of claim 1, and further comprising a plurality of different colored color filters, and means for selectively positioning any one of said plurality of color filters between said light source and said optical collimating means.

9. The apparatus of claim 8, wherein said selective positioning means comprises a rotatable wheel upon which said plurality of color filters are placed in annularly spaced relation thereabout.

10. The apparatus of claim 9, and further comprising means for selectively, automatically rotating said wheel.

11. The apparatus of claim 9 wherein said plurality of color filters are in pairs of colors with the two color filters of a said pair of colors being located diametrically opposite one another on said wheel.

12. A method of applying a color to an iris of an individual, said method comprising the steps of:
    a) providing a light source;
    b) providing a color filter;
    c) providing collimating means for directing a beam of light from said light source, through said color filter, and onto said iris, wherein said color filter is positioned between said light source and said collimating means; and
    d) providing a two-way mirror having first and second, opposite surfaces through which said light beam is directed to impinge upon the iris of an individual viewing him/herself in the surface of said two-way mirror located opposite said collimating means.

13. The method of claim 12, and further comprising a plurality of different colored color filters, and means for selectively positioning any one of said plurality of color filters in the path of said beam of light.

* * * * *